US006825920B2

United States Patent
Lam et al.

(10) Patent No.: US 6,825,920 B2
(45) Date of Patent: Nov. 30, 2004

(54) METHOD AND SYSTEM OF DETERMINING CHAMBER SEASONING CONDITION BY OPTICAL EMISSION

(75) Inventors: Hieu A. Lam, Richardson, TX (US); Hongyu Yue, Austin, TX (US); John Shriner, Allen, TX (US)

(73) Assignee: Tokyo Electron Limited, Tokyo (JP)

( * ) Notice: Subject to any disclaimer, the term of this patent is extended or adjusted under 35 U.S.C. 154(b) by 0 days.

(21) Appl. No.: 10/446,939

(22) Filed: May 29, 2003

(65) Prior Publication Data

US 2004/0008336 A1 Jan. 15, 2004

Related U.S. Application Data

(60) Provisional application No. 60/383,603, filed on May 29, 2002.

(51) Int. Cl.$^7$ ............................ G01N 21/00; G01J 3/28; H05H 1/00
(52) U.S. Cl. ..................... 356/72; 356/328; 356/416; 156/345.24
(58) Field of Search ........................... 356/72, 300, 326, 356/328, 416, 419; 156/345.24

(56) References Cited

U.S. PATENT DOCUMENTS

2003/0052083 A1 * 3/2003 Kim et al. ................. 216/59

* cited by examiner

Primary Examiner—F. L. Evans
(74) Attorney, Agent, or Firm—Oblon, Spivak, McClelland, Maier & Neustadt, P.C.

(57) ABSTRACT

A plasma processing system that comprises a process chamber, a plasma source, a light detection device and a controller. The controller is useful for determining a seasoning state of the plasma processing system. The present invention further provides a method of determining the seasoning state of a plasma processing system comprising the steps of forming a first plasma in the process chamber utilizing the plasma source; measuring a first signal related to light emitted from the first plasma using the light detection device and storing the first signal using the controller; forming a second plasma in the process chamber utilizing the plasma source; measuring a second signal related to light emitted from the second plasma using the light detection device and storing the second signal using the controller; and correlating a change between the first signal and the second signal with a seasoning state of the plasma processing system.

41 Claims, 13 Drawing Sheets

METHOD AND SYSTEM OF DETERMINING CHAMBER SEASONING CONDITION BY OPTICAL EMISSION

CROSS-REFERENCE TO RELATED APPLICATIONS

The present invention claims the benefit of U.S. Provisional Application No. 60/383,603, filed May 29, 2002, the entire contents of which are herein incorporated by reference.

BACKGROUND OF THE INVENTION

1. Field of Invention

The present invention relates to plasma processing and more particularly to a method for determining a seasoning state of a plasma processing system.

2. Description of Related Art

The fabrication of integrated circuits (IC) in the semiconductor industry typically employs plasma to create and assist surface chemistry within a plasma reactor necessary to remove material from and deposit material to a substrate. In general, plasma is formed within the plasma reactor under vacuum conditions by heating electrons to energies sufficient to sustain ionizing collisions with a supplied process gas. Moreover, the heated electrons can have energy sufficient to sustain dissociative collisions, and therefore, a specific set of gases under predetermined conditions (e.g., chamber pressure, gas flow rate, etc.) are chosen to produce a population of charged species and chemically reactive species suitable to the particular process being performed within the chamber (e.g., etching processes where materials are removed from the substrate or deposition processes where materials are added to the substrate).

Typically, during plasma processing such as for example during etch applications, it is necessary to "season" the plasma processing system following a period of process system maintenance, i.e. chamber cleaning, process kit replacement, etc. Prior to initiating production, several substrates, typically of order a hundred wafers, are processed through the plasma processing system in order to form a "seasoning" film on the chamber interior and, thus, facilitate repeatable process performance for the substrates to follow. In general, the number of substrates executed is chosen arbitrarily high to assure proper "seasoning"; however, common practice can lead to excessive cost and time consumption.

SUMMARY OF THE INVENTION

The present invention provides for a plasma processing system that comprises a process chamber, a plasma source and a detection system, wherein the detection system comprises a light detection device and a controller. The controller is useful for determining a seasoning state of the plasma processing system.

The present invention further provides a method of determining the seasoning state of a plasma processing system comprising the steps of forming a first plasma in the process chamber utilizing the plasma source; measuring a first signal related to light emitted from the first plasma using the light detection device and storing the first signal; forming a second plasma in the process chamber utilizing the plasma source; measuring a second signal related to light emitted from the second plasma using the light detection device and storing the second signal; and correlating a change between the first signal and the second signal with a seasoning state of the plasma processing system.

It is an object of the present invention that forming the first plasma corresponds to a first substrate, and forming the second plasma corresponds to a second substrate.

It is another object of the present invention that forming the first plasma corresponds to a first time during the processing of a substrate, and forming the second plasma corresponds to a second time during the processing of the substrate.

It is another object of the present invention that the first plasma is the same as the second plasma.

The present invention further provides an alternate method of determining a seasoning state of a plasma processing system comprising the steps of loading a substrate into the plasma processing system; forming a plasma to facilitate processing of the substrate; measuring a signal related to light emitted from the plasma; comparing the signal with a target signal determined for the plasma processing system; and determining a seasoning state of the plasma processing system from the comparison of the signal with the target signal.

The present invention further provides an alternate method of determining a seasoning state of a plasma processing system comprising the steps of loading a first substrate into the plasma processing system; forming a plasma to facilitate processing of the first substrate; measuring a first signal related to light emitted from the plasma and storing the first signal using the controller; unloading the first substrate; loading a second substrate into the plasma processing system; forming a plasma to facilitate processing of the second substrate; measuring a second signal related to light emitted from the plasma and storing the second signal using the controller; determining a difference signal from the second signal and the first signal; comparing the difference signal with a target signal; and determining a seasoning state of the plasma processing system from the comparing of the difference signal with the target signal.

BRIEF DESCRIPTION OF THE DRAWINGS

These and other advantages of the invention will become more apparent and more readily appreciated from the following detailed description of the exemplary embodiments of the invention taken in conjunction with the accompanying drawings, where.

DETAILED DESCRIPTION OF EXEMPLARY EMBODIMENTS

Figure 1:
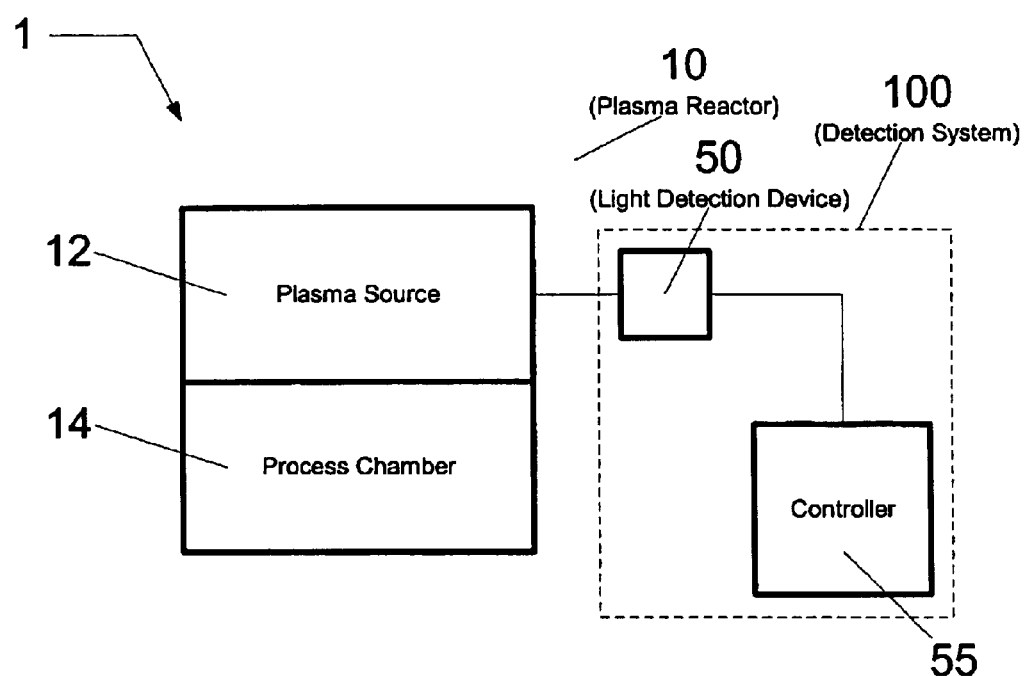
FIG. 1 shows a plasma processing system according to a preferred embodiment of the present invention.

According to an embodiment of the present invention, a plasma processing system 1 is depicted in FIG. 1 comprising a plasma reactor 10, wherein the plasma reactor includes plasma source 12 and process chamber 14, and a detection system 100, wherein the detection system 100 comprises a light detection device 50 and a controller 55. The controller 55 is coupled to the light detection device 50 for measuring a signal related to the light emitted from plasma formed in plasma reactor 10. Moreover, the controller 55 is capable of executing a method of determining a seasoning state of the plasma processing system 1 to be described.

In the illustrated embodiment, plasma processing system 1, depicted in FIG. 1, utilizes a plasma for material processing. Desirably, plasma processing system 1 comprises an etch chamber. Alternately, plasma processing system 1 comprises a deposition chamber such as, for example, a chemical vapor deposition (CVD) system or a physical vapor deposition (PVD) system.

Figure 2:
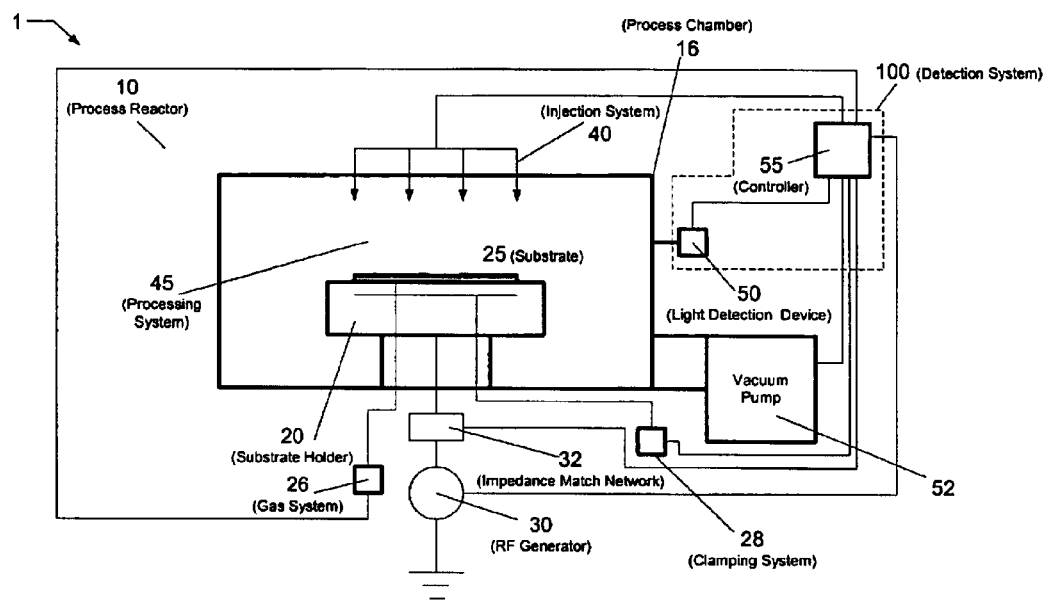
FIG. 2 shows a plasma processing system according to an alternate embodiment of the present invention.

According to the illustrated embodiment of the present invention depicted in FIG. 2, plasma processing system 1 can comprise process reactor 10 with process chamber 16, substrate holder 20, upon which a substrate 25 to be processed can be affixed, gas injection system 40, and vacuum pumping system 52. Substrate 25 can be, for example, a semiconductor substrate, a wafer or a liquid crystal display (LCD). Process chamber 16 can be, for example, configured to facilitate the generation of plasma in processing region 45 adjacent a surface of substrate 25, wherein plasma is formed via collisions between heated electrons and an ionizable gas. An ionizable gas or mixture of gases is introduced via gas injection system 40 and the process pressure is adjusted. For example, a controller 55 can be used to adjust the vacuum pumping system 52. Desirably, plasma is utilized to create materials specific to a predetermined materials process, and to aid either the deposition of material to substrate 25 or the removal of material from the exposed surfaces of substrate 25.

Substrate 25 can be, for example, transferred into and out of process chamber 16 through a slot valve (not shown) and chamber feed-through (not shown) via a robotic substrate transfer system where it is received by substrate lift pins (not shown) housed within substrate holder 20 and mechanically translated by devices housed therein. Once substrate 25 is received from the robotic substrate transfer system, it is lowered to an upper surface of substrate holder 20.

Desirably, the substrate 25 can be, for example, affixed to the substrate holder 20 via an electrostatic clamping system 28. Furthermore, substrate holder 20 can further include a cooling system including a re-circulating coolant flow that receives heat from substrate holder 20 and transfers heat to a heat exchanger system (not shown), or when heating, transfers heat from the heat exchanger system. Moreover, gas can be delivered to the back-side of the substrate via a backside gas system 26 to improve the gas-gap thermal conductance between substrate 25 and substrate holder 20. Such a system can be utilized when temperature control of the substrate is required at elevated or reduced temperatures. For example, temperature control of the substrate can be useful at temperatures in excess of the steady-state temperature achieved due to a balance of the heat flux delivered to the substrate 25 from the plasma and the heat flux removed from substrate 25 by conduction to the substrate holder 20. In other embodiments, heating elements, such as resistive heating elements, or thermoelectric heaters/coolers can be included.

In the illustrated embodiment, shown in FIG. 2, substrate holder 20 can, for example, further serve as an electrode through which RF power is coupled to plasma in processing region 45. For example, substrate holder 20 is electrically biased at a RF voltage via the transmission of RF power from RF generator 30 through impedance match network 32 to substrate holder 20. The RF bias can serve to heat electrons and, thereby, form and maintain plasma. In this configuration, the system can operate as a reactive ion etch (RIE) reactor, wherein the chamber and upper gas injection electrode (not shown) serve as ground surfaces. A typical frequency for the RF bias can range from 1 MHz to 100 MHz and is preferably 13.56 MHz. RF systems for plasma processing are well known to those skilled in the art.

Alternately, RF power is applied to the substrate holder electrode at multiple frequencies. Furthermore, impedance match network 32 serves to maximize the transfer of RF power to plasma in processing chamber 10 by minimizing the reflected power. Match network topologies (e.g. L-type, π-type, T-type, etc.) and automatic control methods are well known to those skilled in the art.

With continuing reference to FIG. 2, process gas can be, for example, introduced to processing region 45 through gas injection system 40. Process gas can, for example, comprise a mixture of gases such as argon, $CF_4$ and $O_2$, or argon, $C_4F_8$ and $O_2$ for oxide etch applications, or other chemistries such as, for example, $O_2/CO/Ar/C_4F_8$, $O_2/CO/AR/C_5F_8$, $O_2/CO/Ar/C_4F_6$, $O_2/Ar/C_4F_6$, $N_2/H_2$. Gas injection system 40 can comprise a showerhead, wherein process gas is supplied from a gas delivery system (not shown) to the processing region 45 through a gas injection plenum (not shown), a series of baffle plates (not shown) and a multi-orifice showerhead gas injection plate (not shown). Gas injection systems are well known to those of skill in the art.

As described in FIG. 1, a light detection device 50 is coupled to process chamber 16 to monitor light emitted from the plasma in processing region 45. The light detection device 50 can include a detector such as, for example, a (silicon) photodiode or a photomultiplier tube (PMT) for measuring the total light intensity emitted from the plasma. It can further comprise an optical filter such as, for example, a narrow-band interference filter. In an alternate embodiment, light detection device 50 can comprise a line CCD (charge coupled device) or CID (charge injection device) array and a light dispersing device such as, for example, a grating or a prism. Additionally, light detection device 50 can be a monochromator (grating/detector system) for measuring light at a given wavelength or a spectrometer (with a rotating grating) for measuring the light spectrum such as, for example, the device described in U.S. Pat. No.

5,888,337. Similarly, light detection device 50 can be, for example, a high resolution OES sensor from Peak Sensor Systems. Such an OES sensor has a broad spectrum that spans the ultraviolet (UV), visible (VIS) and near infrared (NIR) light spectrums. The resolution is approximately 1.4 Angstroms, that is, the sensor is capable of collecting 5550 wavelengths from 240 to 1000 nm. The sensor is equipped with high sensitivity miniature fiber optic UV-VIS-NIR spectrometers which are, in turn, integrated with 2048 pixel linear CCD arrays. The spectrometers receive light transmitted through single and bundled optical fibers, where the light output from the optical fibers is dispersed across the line CCD array using a fixed grating. Similar to the configuration described above, light emitting through an optical vacuum window is focused onto the input end of the optical fibers via a convex spherical lens. Three spectrometers, each specifically tuned for a given spectral range (UV, VIS and NIR), form a sensor for a process chamber. Each spectrometer includes an independent A/D converter. And lastly, depending upon the sensor utilization, a full emission spectrum can be recorded every 0.1 to 1.0 seconds.

Vacuum pump system 52 can, for example, include a turbo-molecular vacuum pump (TMP) capable of a pumping speed up to 5000 liters per second (and greater) and a gate valve for throttling the chamber pressure. In conventional plasma processing devices utilized for dry plasma etch, a 1000 to 3000 liter per second TMP is generally employed. TMPs are useful for low pressure processing, typically less than 50 mTorr. At higher pressures, the TMP pumping speed falls off dramatically. For high pressure processing (i.e. greater than 100 mTorr), a mechanical booster pump and dry roughing pump can be used. Furthermore, a device for monitoring chamber pressure (not shown) is coupled to the process chamber 16. The pressure measuring device can be, for example, a Type 628B Baratron absolute capacitance manometer commercially available from MKS Instruments, Inc. (Andover, Mass.).

Controller 55 comprises a microprocessor, memory, and a digital I/O port capable of generating control voltages sufficient to communicate and activate inputs to plasma processing system 1 as well as monitor outputs from plasma processing system 1. Moreover, controller 55 is coupled to and exchanges information with RF generator 30, impedance match network 32, gas injection system 40, vacuum pump system 52, backside gas delivery system 26, electrostatic clamping system 28, and light detection device 50. A program stored in the memory is utilized to activate the inputs to the aforementioned components of a material processing system 1 according to a stored process recipe. One example of controller 55 is a DELL PRECISION WORKSTATION 530™, available from Dell Corporation, Austin, Tex.

Figure 3:
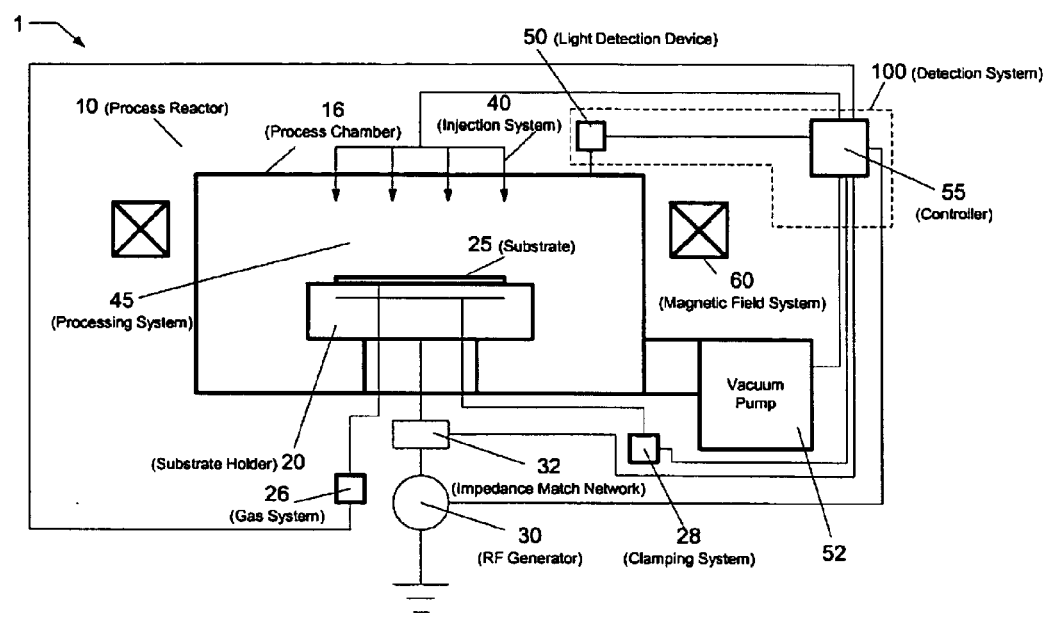
FIG. 3 shows a plasma processing system according to another embodiment of the present invention.

In the illustrated embodiment, shown in FIG. 3, the plasma processing system 1 can, for example, further comprise either a mechanically or electrically rotating dc magnetic field system 60, in order to potentially increase plasma density and/or improve plasma processing uniformity, in addition to those components described with reference to FIGS. 1 and 2. Moreover, controller 55 is communicatively coupled to rotating magnetic field system 60 in order to regulate the speed of rotation and field strength. The design and implementation of a rotating magnetic field is well known to those skilled in the art.

Figure 4:
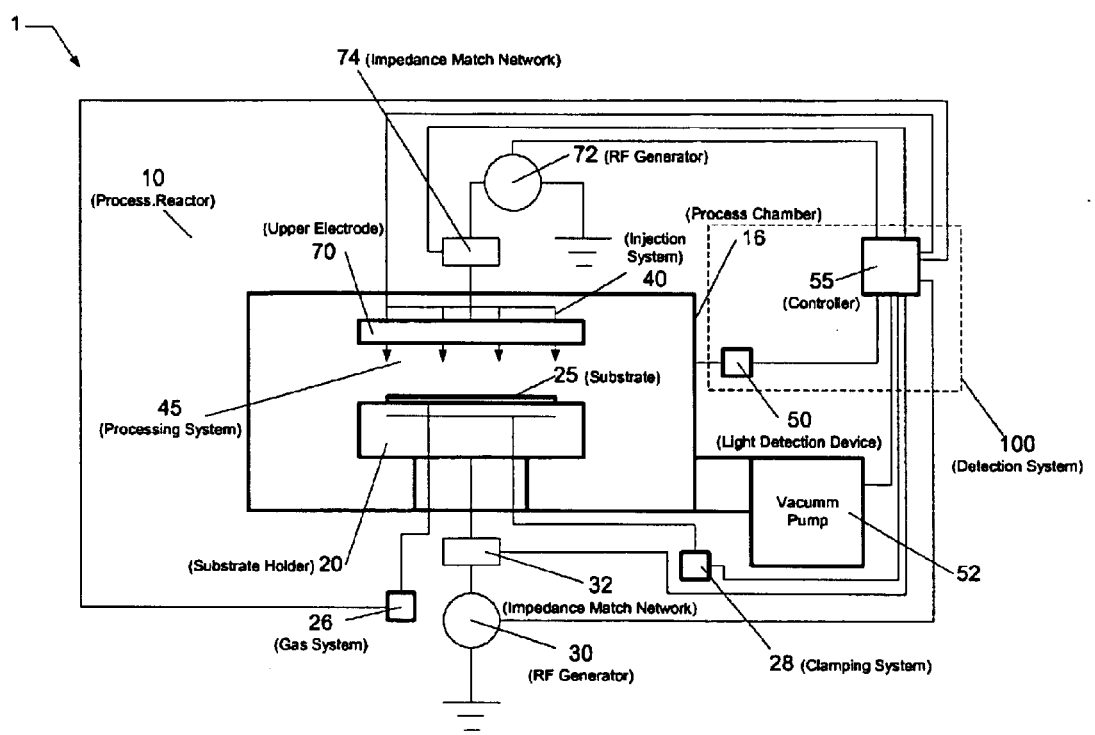
FIG. 4 shows a plasma processing system according to another embodiment of the present invention.

In the illustrated embodiment, shown in FIG. 4, the plasma processing system 1 of FIGS. 1 and 2 can, for example, further comprise an upper electrode 70 to which RF power can be coupled from RF generator 72 through impedance match network 74. A typical frequency for the application of RF power to the upper electrode can range from 10 MHz to 200 MHz and is preferably 60 MHz. Additionally, a typical frequency for the application of power to the lower electrode can range from 0.1 MHz to 30 MHz and is preferably 2 MHz. Moreover, controller 55 is coupled to RF generator 72 and impedance match network 74 in order to control the application of RF power to upper electrode 70. The design and implementation of an upper electrode is well known to those skilled in the art.

Figure 5:
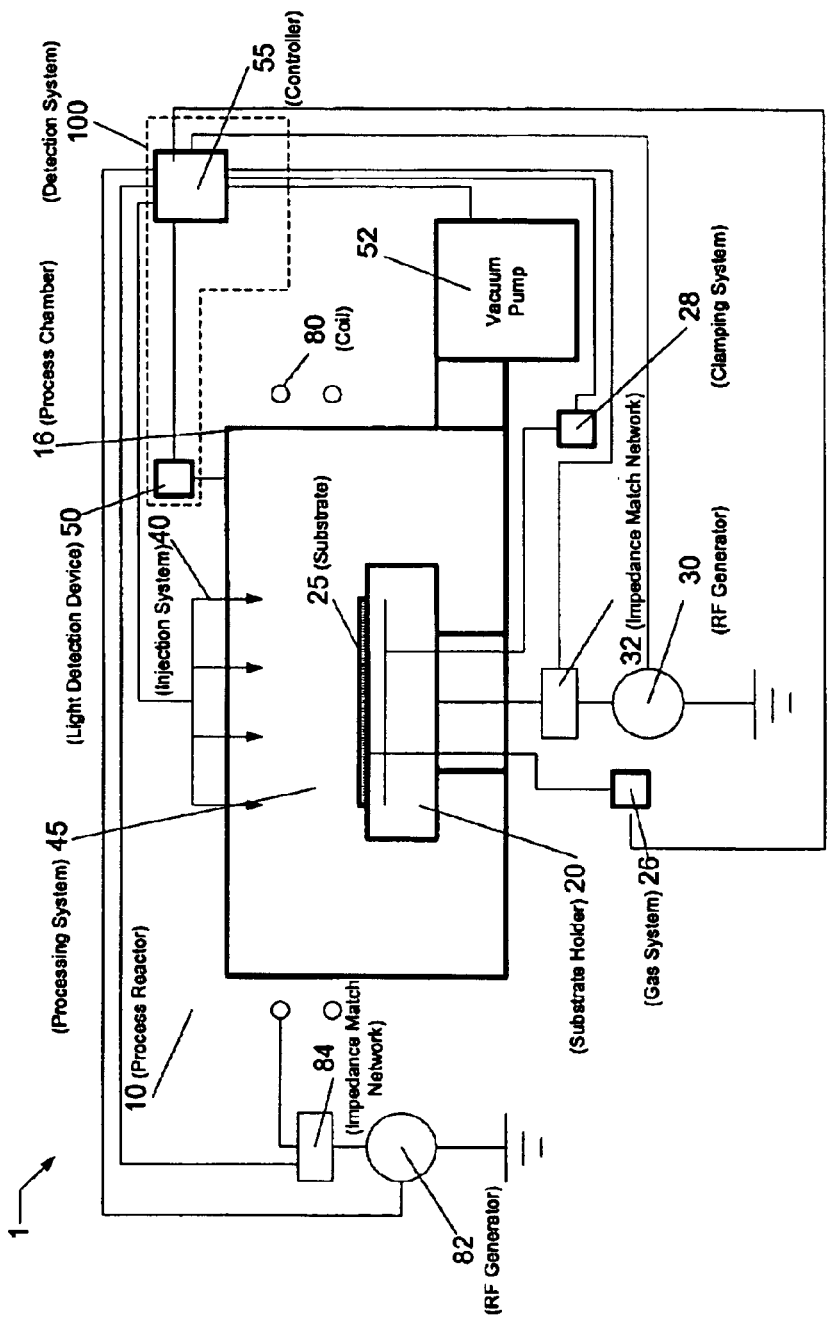
FIG. 5 shows a plasma processing system according to an additional embodiment of the present invention.

In the illustrated embodiment, shown in FIG. 5, the plasma processing system of FIG. 1 can, for example, further comprise an inductive coil 80 to which RF power is coupled via RF generator 82 through impedance match network 84. RF power is inductively coupled from inductive coil 80 through dielectric window (not shown) to plasma processing region 45. A typical frequency for the application of RF power to the inductive coil 80 can range from 10 MHz to 100 MHz and is preferably 13.56 MHz. Similarly, a typical frequency for the application of power to the chuck electrode can range from 0.1 MHz to 30 MHz and is preferably 13.56 MHz. In addition, a slotted Faraday shield (not shown) can be employed to reduce capacitive coupling between the inductive coil 80 and plasma. Moreover, controller 55 is coupled to RF generator 82 and impedance match network 84 in order to control the application of power to inductive coil 80. In an alternate embodiment, inductive coil 80 can be a "spiral" coil or "pancake" coil in communication with the plasma processing region from above as in a transformer coupled plasma (TCP) reactor. The design and implementation of an inductively coupled plasma (ICP) source and/or transformer coupled plasma (TCP) source is well known to those skilled in the art.

Alternately, the plasma can be formed using electron cyclotron resonance (ECR). In yet another embodiment, the plasma is formed from the launching of a Helicon wave. In yet another embodiment, the plasma is formed from a propagating surface wave. Each plasma source described above is well known to those skilled in the art.

Figure 6:
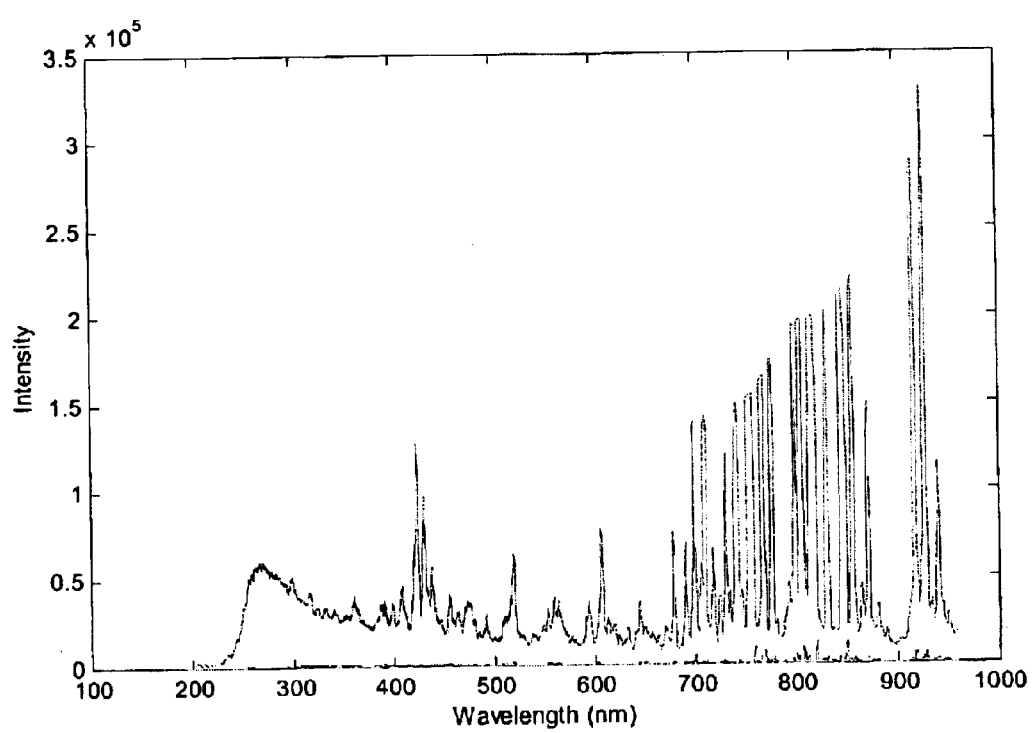
FIG. 6 presents a set of typical optical emission spectra from several substrates processed in a plasma processing system described in FIG. 1.

Using a plasma processing system 1 as described in FIG. 1, emission spectra from twenty five (25) substrate runs are overlaid in FIG. 6 wherein the twenty five substrate runs follow a chamber clean preceding the first substrate. Each spectrum represents an ensemble averaged emission spectrum for a one minute etch process. During the one minute etch process, emission spectra are sampled every three seconds until twenty sample spectra are obtained, and then they are, in turn, ensemble averaged. In general, visual inspection of emission spectra during a one minute etch process indicates very little variation. Moreover, it is observed that the run-to-run variation is small as well, as shown in FIG. 6.

Figure 7A:
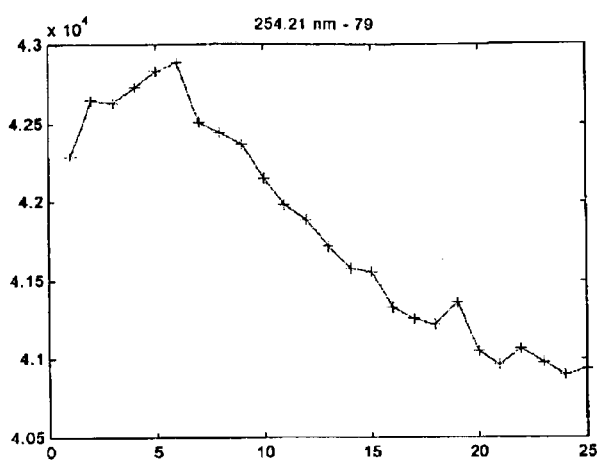
FIG. 7A presents a signal related to light intensity at a first wavelength as a function of substrate number.
Figure 7B:
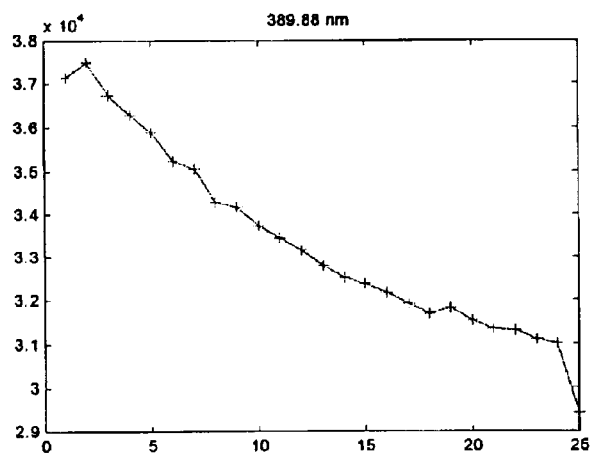
FIG. 7B presents a signal related to light intensity at a second wavelength as a function of substrate number.
Figure 7C:
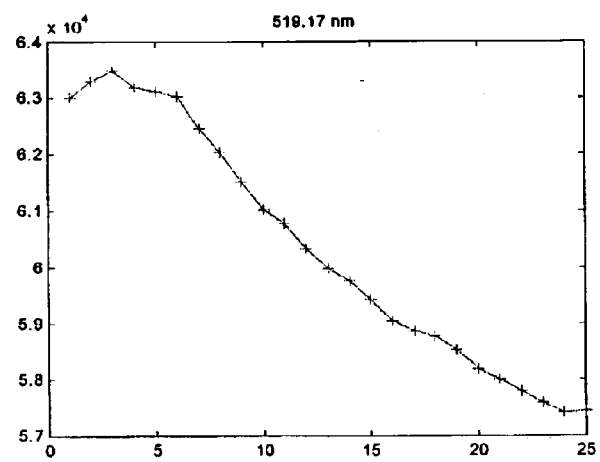
FIG. 7C presents a signal related to light intensity at a third wavelength as a function of substrate number.

However, for some wavelengths, a substantive run-to-run variation in emission intensity can be observed. For example, FIGS. 7A through 7C present emission intensity as a function of substrate number for wavelengths of 254.21 nm, 389.88 nm and 519.17 nm, respectively. In each case, the light intensity decays with increasing substrate number and gradually "flattens" out between wafer numbers 15 and 25 (see FIGS. 7A and 7B). As described above, a specific process chemistry is selected per the application. Therein, various chemical species will be known to be present and can give some inference as to where in the emission spectrum to look to determine a signal useable for determining the seasoning state of a plasma processing system. In general, fairly tedious efforts by one skilled in the art of optical diagnostics and chemistry can identify spectral regions of interest. However, it is further possible to utilize Design of Experiment (DOE) techniques to establish a "good" signal for interpretation.

Several criteria can be utilized to determine when the plasma processing system 1 is properly "seasoned". For example, the seasoning of the plasma processing system 1 can be determined to be complete when: (1) the measured optical signal falls to a value less than a pre-determined target signal, or (2) the slope of the measured optical signal from run-to-run falls below some pre-determined value or falls to within a specified distance from zero-slope. Utilizing these criteria and the data presented in FIGS. 7A and 7B, one can conclude that the plasma processing system 1 of FIG. 1 is "seasoned" after approximately fifteen to twenty substrate runs.

However, in some cases, no discernible change can be made in the observed signal and a more robust approach to identifying a "seasoning" optical signal is required. When encountering large sets of data involving a substantive number of variables, multivariate analysis (MVA) is often applied. For example, one such MVA technique includes Principal Components Analysis (PCA). In PCA, a model can be assembled to extract from a large set of data, a signal exhibiting the greatest variance in the multi-dimensional variable space.

For example, a PCA model for the twenty five substrate runs shown in FIG. 6 can be assembled. Each spectrum for each substrate run comprises the ensembled averaged emission intensity at 1024 discrete wavelengths in the UV-VIS-NIR spectrum using the OES sensor described above. Each ensemble averaged emission spectrum for a given substrate run is stored as a row in a matrix $\overline{X}$ and, hence, once the matrix $\overline{X}$ is assembled, each row represents a different substrate number and each column represents a different emission intensity for a given wavelength. Therefore, in this example, matrix $\overline{X}$ is a rectangular matrix of dimensions 25 by 1024, or more generally, m by n. Once the data is stored in the matrix, the data is preferably mean-centered and/or normalized, if desired. The process of mean-centering the data stored in a matrix column involves computing a mean value of the column elements and subtracting the mean value from each element. Moreover, the data residing in a column of the matrix can be normalized by determining the standard deviation of the data in the column.

Using the PCA technique, the correlation structure within matrix $\overline{X}$ is determined by approximating matrix $\overline{X}$ with a matrix product ($\overline{TP^T}$) of lower dimensions plus an error matrix $\overline{E}$, viz.

$$\overline{X} = \overline{TP^T} + \overline{E}, \quad (1)$$

where $\overline{T}$ is a (m by p) matrix of scores that summarizes the $\overline{X}$ variables and $\overline{P}$ is a (n by p, where p≤n) matrix of loadings showing the influence of the variables.

In general, the loadings matrix $\overline{P}$ can be shown to comprise the eigenvectors of the covariance matrix of $\overline{X}$, where the covariance matrix $\overline{S}$ can be shown to be $$\overline{S} = \overline{X^T X}. \quad (2)$$

The covariance matrix $\overline{S}$ is a real, symmetric matrix and, therefore, it can be described as $$\overline{S} = \overline{U \Lambda U^T}, \quad (3)$$

where the real, symmetric eigenvector matrix $\overline{U}$ comprises the normalized eigenvectors as columns and $\overline{\Lambda}$ is a diagonal matrix comprising the eigenvalues corresponding to each eigenvector along the diagonal. Using equations (1) and (3) (for a full matrix of p=n; i.e. no error matrix), one can show that $$\overline{P} = \overline{U} \quad (4)$$

and $$\overline{T^T T} = \overline{\Lambda}. \quad (5)$$

A consequence of the above eigenanalysis is that each eigenvalue represents the variance of the data in the direction of the corresponding eigenvector within n-dimensional space. Hence, the largest eigenvalue corresponds to the greatest variance in the data within the n-dimensional space whereas the smallest eigenvalue represents the smallest variance in the data. By definition, all eigenvectors are orthogonal, and therefore, the second largest eigenvalue corresponds to the second greatest variance in the data in the direction of the corresponding eigenvector which is, of course, normal to the direction of the first eigenvector. In general, for such analysis, the first three to four largest eigenvalues are chosen to approximate the data and, as a result of the approximation, an error $\overline{E}$ is introduced to the representation in equation (1). In summary, once the set of eigenvalues and their corresponding eigenvectors are determined, a set of the largest eigenvalues can be chosen and the error matrix $\overline{E}$ of equation (1) can be determined.

An example of commercially available software which supports PCA modeling is SIMCA-P 8.0; for further details, see the User's Manual (*User Guide to SIMCA-P 8.0: A new standard in multivariate data analysis*, Umetrics AB, Version 8.0, September 1999). The contents of the manual are incorporated herein by reference. Using SIMCA-P 8.0, for example, with the data of FIG. 6, one can determine the scores matrix $\overline{T}$ and the loadings matrix $\overline{P}$, as well as additional information regarding the ability of each component to describe each variable in $\overline{X}$ and the total variation of each variable in $\overline{X}$ by a component.

Figure 8:
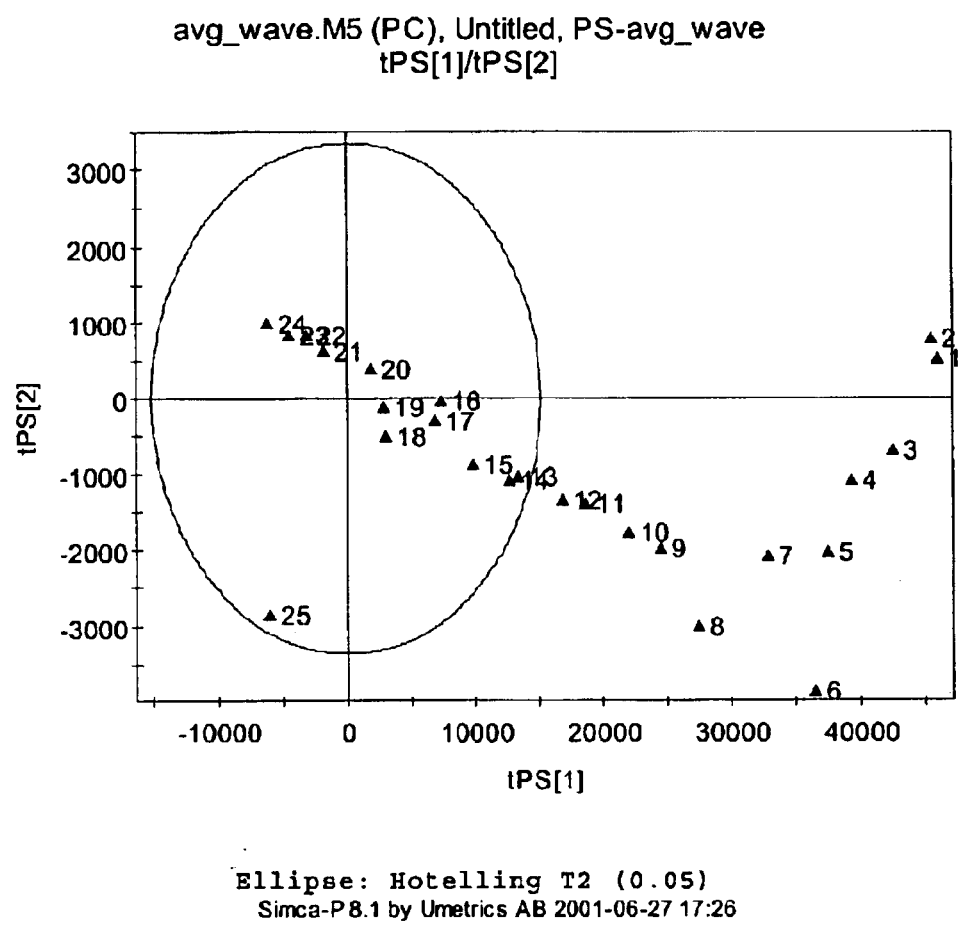
FIG. 8 presents the scores corresponding to each spatial component in t(1), t(2) space provided in the exemplary data of FIG. 6.
Figure 9:
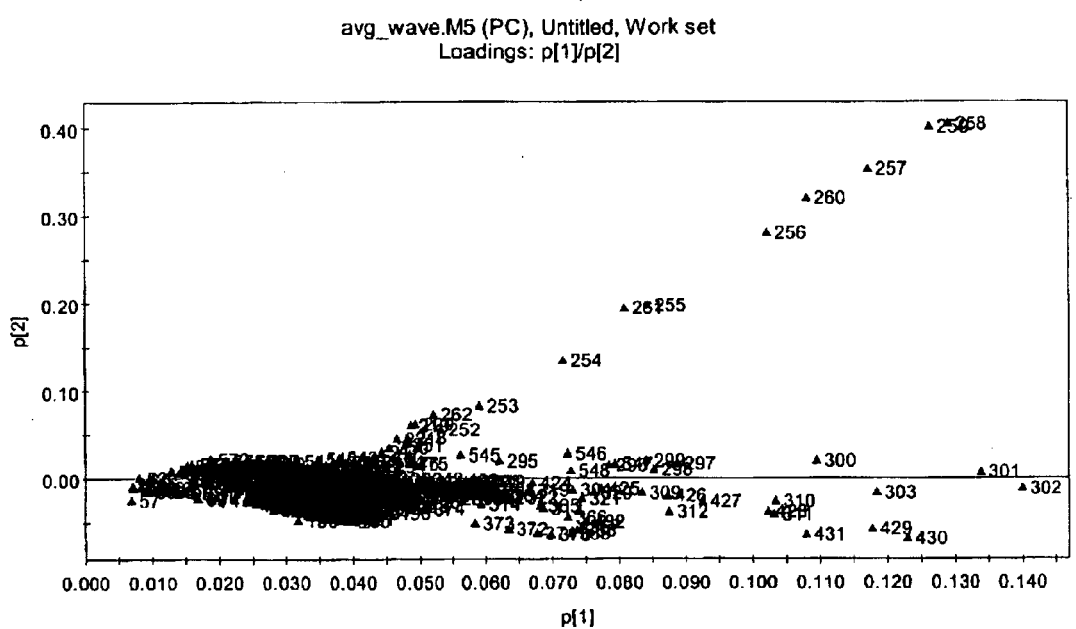
FIG. 9 presents the loadings for each variable in p(1), p(2) space provided in the exemplary data of FIG. 6.

FIG. 8 presents the scores for each spatial component in t(1), t(2) space provided in the exemplary data of FIG. 6, and FIG. 9 presents the loadings for each variable in p(1), p(2) space provided in the exemplary data of FIG. 6. The data of FIG. 8, in t(1)–t(2) space, displays the data variability through a measure of dispersion from the data center where, in particular, emission data from substrate numbers 1 through 10 are shown to reside in a substantially different space than the data from the remaining substrate runs. This result indicates one should investigate using a latter portion of the substrate runs for building a PCA model to describe a "seasoned" chamber; i.e. the chemical conditions of the processing system are substantially changing during the first 5 to 10 substrate runs. From FIG. 9, one can determine which regions of the emission spectrum exhibit appreciable variation that could be potentially utilized for monitoring the seasoning state of the plasma processing system 1.

In FIG. 8, one can determine that the plasma processing system 1 is "seasoned" following the fifteenth substrate run. Therefore, the remaining ten substrate runs can be representative of a "seasoned" plasma processing system and, hence, be used to assemble a seasoning model (or PCA model) using SIMCA-P. Conversely, the first fifteen substrate runs can be representative of an "unseasoned" plasma processing system. Following the discussion above, the data matrix $\overline{X}$ can be assembled using the spectra from the last ten substrate runs. Upon completion, the principal components and scores can be computed as discussed in FIGS. 8 and 9. Choosing the three to four largest eigenvalues and corresponding eigenvectors, one can assemble the seasoning model (or PCA model) from these principal components (i.e., eigenvectors). Using these principal components, each spectrum ascertained from a substrate run can be projected thereon to determine a "measured" score (see equation (1)). From the measured scores and model scores, a distance from the model can be computed. In SIMCA-P, a parameter entitled 'DModXPS' can be output which is a combined measure of the residual standard deviation of the sample and score distances (distance of the new score(s) to the normal score range of that model, if the score(s) is outside that range).

Figure 10:
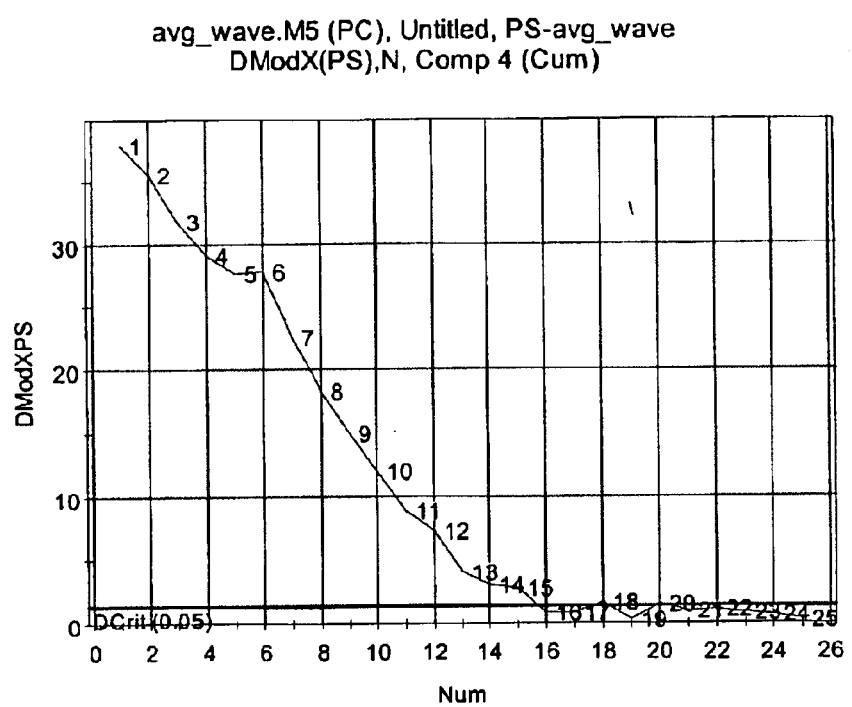
FIG. 10 shows the variation of a model signal with wafer number for determining a seasoning state of the plasma processing system in FIG. 1.

FIG. 10 presents a signal related to the optical emission from the plasma processing system, determined from the PCA model, as a function of substrate number. In this case, the signal is represented by the parameter DModXPS output from SIMCA-P. Clearly, the signal exhibits a distinct change in behavior beyond the fifteenth substrate run. Using at least one of the criteria described above, the substrate when plasma processing system 1 achieves a seasoned state can be determined.

Furthermore, controller 55 can be capable of controlling the seasoning state of a plasma processing system 1. The method of controlling the seasoning state can comprise at least one of executing a seasoning process recipe and/or executing a series of seasoning substrates. In one embodiment as discussed above, a series of seasoning substrates such as, for example, blank substrates coated with a photoresist layer, are executed within the plasma processing system utilizing a seasoning process recipe such as, for example, a standard etch process recipe. In an alternate embodiment, the seasoning state can be controlled by executing a wafer-less seasoning process recipe. For example, a waterless seasoning process recipe comprising a conditioning gas including a fluorine-containing gas and a carbon-containing gas is described in U.S. Pat. No. 6,350,697 issued to Lam Research Corporation.

Figure 11:
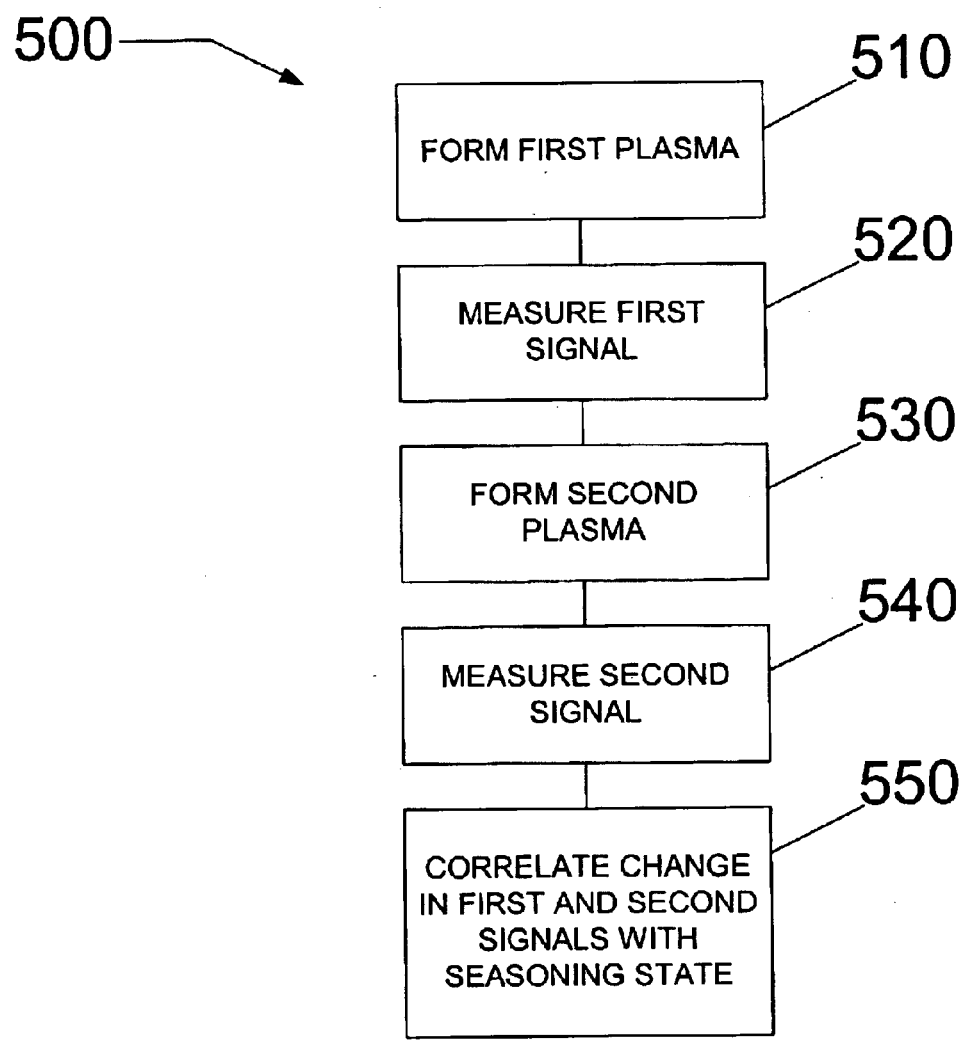
FIG. 11 presents a method of determining a seasoning state of the plasma processing system of FIG. 1 according to an embodiment of the present invention.

With reference now to FIG. 11, a method of determining the seasoning state of a plasma processing system is presented. A flowchart 500 describing the method begins with step 510 wherein plasma is formed in the processing region of a plasma processing system. In step 520, a first signal related to the light emitted from the plasma is measured using a light detection device and stored using a controller. The signal can comprise at least one of a light intensity, a light spectrum, a spectral light intensity, a linear combination of light intensities, a nonlinear combination of light intensities, a linear combination of spectral light intensities, a nonlinear combination of spectral light intensities, an output from a MVA model such as, for example, an output from a PCA model.

In step 530, a second plasma is formed and, in step 540, a second signal related to the light emitted from the plasma is measured using the light detection device and stored using the controller. As before, the signal can comprise any one of the above light intensities, or mathematical manipulations thereof.

In one embodiment, the first plasma is formed during a processing of a first substrate, and the second plasma is formed during a processing of a second substrate. In an alternate embodiment, the first plasma is formed at a first time during the processing of a substrate, and the second plasma is formed at a second time during the processing of a substrate. In an alternate embodiment, the first and second plasmas are the same plasma.

In step 540, a change in the first and second signals is determined, and the change is correlated with a seasoning state of the plasma processing system 1. For example, the change in the first and second signals can provide a difference, and when the difference in signals is sufficiently small, the plasma processing system 1 is seasoned. Moreover, the difference in signals can be a slope, and once the slope becomes less than a pre-determined value or becomes sufficiently close to zero-slope (see FIG. 10), then the plasma processing system is determined to be seasoned and ready for production substrates.

Figure 12:
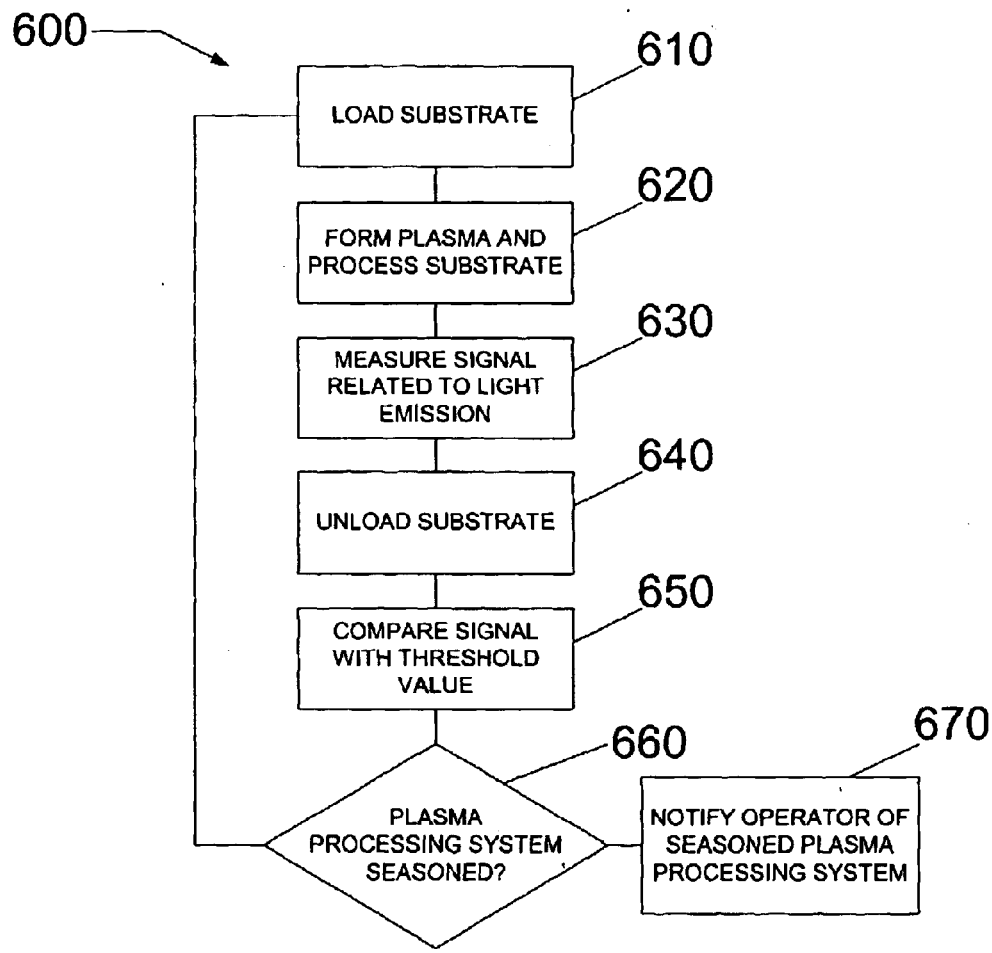
FIG. 12 presents a method of determining a seasoning state of the plasma processing system of FIG. 1 according to another embodiment of the present invention.

With reference now to FIG. 12, an alternate method of determining the seasoning state of a plasma processing system is presented. A flowchart 600 describing the method begins with step 610 wherein a substrate (i.e. semiconductor wafer, LCD, etc.) is loaded into the plasma processing system for chamber seasoning. Once the substrate is loaded, in step 620, a plasma is formed and the substrate is processed. In step 630, at least one signal related to the light emitted from the plasma is measured and the at least one signal is stored using the controller. The signal can comprise at least one of a light intensity, a light spectrum, a spectral light intensity, a linear combination of light intensities, a nonlinear combination of light intensities, a linear combination of spectral light intensities, a nonlinear combination of spectral light intensities, an output from a MVA model such as, for example, an output from a PCA model.

In step 640, the substrate is unloaded and, in step 650, either before, after or concurrently with this action, the at least one signal is compared with a predetermined target signal. Using collected data (e.g., the data of FIGS. 7A through 7C and FIG. 10), when the signal becomes less than the pre-determined target signal then the plasma processing system is determined to be seasoned. For example, with reference to FIG. 10, when the signal DModXPS becomes less than a value of two, then the plasma processing system is seasoned. In step 660, if the plasma processing system is seasoned, then an operator is notified of the plasma processing system condition in step 670. In step 660, if the plasma processing system is not seasoned, then another substrate is loaded in step 610 and steps 620 through 660 are repeated.

Figure 13:
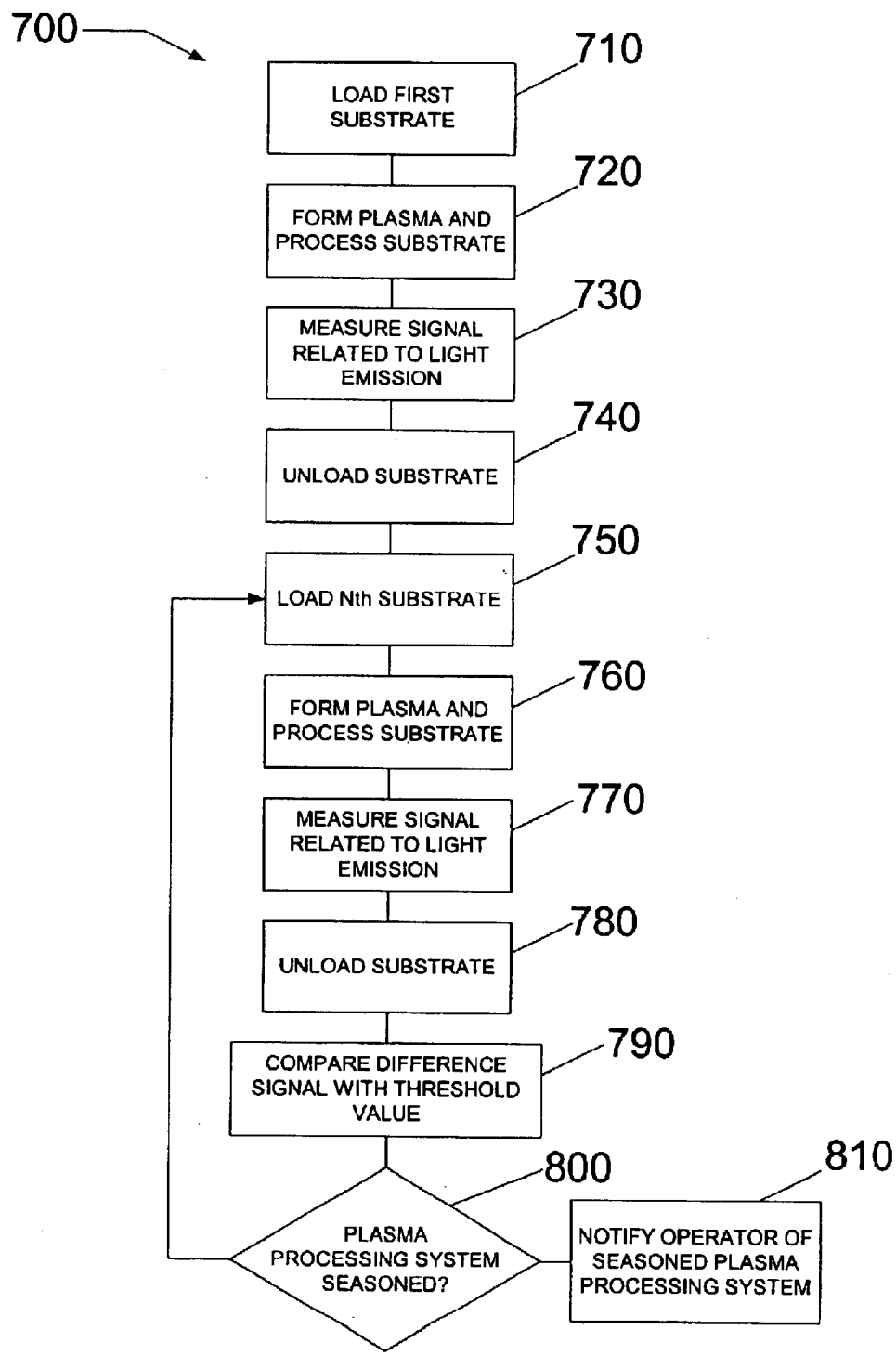
FIG. 13 presents a method of determining a seasoning state of the plasma processing system of FIG. 1 according to another embodiment of the present invention.

With reference now to FIG. 13, an alternate method of determining the seasoning state of a plasma processing system is presented. A flowchart 700 describing the method begins with step 710 wherein a first substrate (e.g., semiconductor wafer, LCD), following maintenance of the plasma processing system (e.g., chamber cleaning, process kit replacement), is loaded into the plasma processing system for chamber seasoning. Once the first substrate is loaded, in step 720, a plasma is formed and the substrate is processed. In step 730, at least one signal related to the light emitted from the plasma is measured and the at least one signal is stored using the controller. The signal can comprise at least one of a light intensity, a light spectrum, a spectral light intensity, a linear combination of light intensities, a nonlinear combination of light intensities, a linear combination of spectral light intensities, a nonlinear combination of spectral light intensities, an output from a MVA model such as, for example, an output from a PCA model. Following the completion of the process, the first substrate is unloaded in step 740.

In step 750, an $N^{th}$ substrate is loaded into the plasma processing system. The $N^{th}$ substrate represents the next substrate in order, i.e. the second, third, fourth, . . . , $N^{th}$. Once the first substrate is loaded, in step 760, a plasma is formed and the substrate is processed. In step 770, at least one signal related to the light emitted from the plasma is measured and the at least one signal is stored using the controller.

In step 780, the substrate is unloaded and, in step 790, either before, after or concurrently with the action of step 780, the at least one signal from the current (i.e., the Nth) substrate is compared with the at least one signal from at least one of the preceding substrates (e.g., the N−1$^{st}$) to form at least one difference signal. In step 790, the difference signal is then compared with a predetermined target signal. For example, the difference signal can be a slope such as, for instance, a backward difference slope of the DModXPS data presented in FIG. 10, viz.

$$SLOPE = \frac{\Delta(DModXPS)}{\Delta N} = \frac{(DModXPS)_N - (DModXPS)_{N-1}}{1}, \quad (6)$$

where ΔN is the change in substrate number. When for example, with reference to FIG. 10, the SLOPE (Eqn. 6) becomes less than a value such as, for instance, two, then the plasma processing system is seasoned. In step 800, if the plasma processing system is seasoned, then an operator is notified of the plasma processing system condition in step 810. In step 800, if the plasma processing system is not seasoned, then another substrate is loaded in step 750 and steps 760 through 800 are repeated.

Although only certain exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

What is claimed is:

1. A plasma processing system comprising:
   a plasma reactor;
   a light detection device coupled to said plasma reactor to receive light emitted from a plasma formed within said plasma reactor; and
   a controller coupled to said light detection device, said controller configured to measure a signal related to the received light detected by the light detection device and to correlate a change between the measured signal and a target signal corresponding to a seasoning state of said plasma reactor, wherein the measured signal related to e received light is a product of multivariate analysis.

2. The plasma processing system according to claim 1, wherein said light detection device comprises a photodetector.

3. The plasma processing system according to claim 2, wherein said light detection device further comprises at least one of an optical filter and a grating.

4. The plasma processing system according to claim 1, wherein said light detection device comprises at least one of a spectrometer and a monochromator.

5. The plasma processing system according to claim 1, wherein the measured signal related to the received light comprises at least one of a light intensity, a spectral light intensity, and a light spectrum.

6. The plasma processing system according to claim 1, wherein said seasoning state of said plasma reactor comprises whether the plasma reactor is seasoned.

7. The plasma processing system according to claim 1, wherein said controller determines that the seasoning state of the plasma reactor corresponds to a seasoned plasma reactor when a change between said signal and a target signal comprises said signal being of a value less than a value of said target signal.

8. The plasma processing system according to claim 1, wherein said multivariate analysis comprises principal components analysis.

9. The plasma processing system according to claim 8, wherein a result of said principal components analysis is a set of scores.

10. The plasma processing system according to claim 9, wherein said controller further comprises a correlator configured to determine a difference signal between said set of scores for the measured signal and a set of scores for said target signal in order to determine said seasoning state of said plasma reactor.

11. The plasma processing system according to claim 10, wherein said seasoning state corresponds to a seasoned plasma reactor when said difference signal is substantially close to a value of zero.

12. The plasma processing system according to claim 1, wherein said controller further comprises a seasoning state controller.

13. The plasma processing system according to claim 12, wherein said seasoning state controller comprises a controller configured to use at least one of a seasoning process recipe and a seasoning substrate.

14. A method of determining a seasoning state of a plasma processing system, wherein said plasma processing system comprises a process chamber, a plasma source, a light detection device and a controller, said method comprises:
   forming a first plasma in said process chamber utilizing said plasma source;
   measuring a first signal related to light emitted from said first plasma using said light detection device and storing said first signal;
   forming a second plasma in said process chamber utilizing said plasma source;
   measuring a second signal related to light emitted from said second p1 a using said light detection device and storing said second signal using said controller; and
   correlating a change between said first signal and said second signal with a seasoning state of said plasma processing system, wherein the first signal or the second signal, or both the first and second signal is provided as a product of multivariate analysis.

15. The method according to claim 14, wherein said forming said first plasma corresponds to a first substrate, and said forming said second plasma corresponds to a second substrate.

16. The method according to claim 14, wherein said forming said first plasma corresponds to a first period of time during processing a substrate, and said forming said second plasma corresponds to a second period of time during processing another substrate.

17. The method according to claim 14, wherein said first signal and said second signal are at least one of a light intensity, a spectral light intensity and a light spectrum.

18. The method according to claim 14, wherein said correlating said change between said first signal and said second signal with said seasoning state of said plasma processing system comprises forming a difference signal from said first and said second signals and determining said seasoning state of said plasma processing system from a magnitude of said difference signal.

19. The method according to claim 18, wherein said plasma processing system is seasoned when said magnitude of said difference signal is less than one.

20. A method of determining a seasoning state of a plasma processing system, wherein said plasma processing system comprises a process chamber, a plasma source, a light detection device and a controller, said method comprises:

forming a plasma in said process chamber utilizing said plasma source;

measuring a first signal related to light emitted from said plasma using said light detection device and storing said first signal;

measuring a second signal related to light emitted from said plasma using said light detection device and storing said second signal using said controller; and correlating a change between said first signal and said second signal with a seasoning state of said plasma processing system, wherein the first signal or the second signal, or both the first and second signal is provided as a product of multivariate analysis.

21. A method of determining a seasoning state of a plasma processing system, wherein said plasma processing system comprises a process chamber, a plasma source, a light detection device and a controller, said method comprises:

loading a substrate into said plasma processing system;

forming a plasma to facilitate processing of said substrate;

measuring a signal related to light emitted from said plasma;

comparing the measured signal with a target signal determined for said plasma processing system; and determining a seasoning state of said plasma processing system from a result of said comparing of the measured signal with said target signal, wherein the measure signal is a product of multivariate analysis.

22. The method according to claim 21, wherein the measured signal is at least one of a light intensity, a spectral light intensity and a light spectrum.

23. The method according to claim 21, wherein said seasoning state of said plasma processing system comprises whether said plasma processing system is seasoned.

24. The method according to claim 21, wherein said multivariate analysis comprises principal components analysis.

25. The method according to claim 24, wherein a result of said principal components analysis is a set of scores.

26. The method according to claim 21, wherein said comparing the measured signal with a target signal comprises determining difference signal between said set of scores for the measured signal and a set of scores for aid target signal.

27. The method according to claim 26, wherein said determining said seasoning state of said plasma processing system comprises determining that said plasma processing system is seasoned when said difference signal is substantially close to a value of zero.

28. The method according to claim 21, wherein said determining said seasoning state of said plasma processing system comprises determining that said plasma processing system is seasoned when said measured signal is less than said target signal.

29. A method of determining a seasoning state of a plasma processing system, wherein said plasma processing system comprises process chamber, a plasma source, a light detection device and a controller, said meth comprises:

loading a first substrate into said plasma processing system;

forming a first plasma to facilitate processing of said first substrate;

measuring a first signal related to light emitted from first plasma and storing said first signal using said controller;

unloading said first substrate;

loading a second substrate into said plasma processing system;

forming a second plasma to facilitate processing of said second substrate;

measuring a second signal related to light emitted from said second plasma and storing said second signal using said controller;

determining a difference signal from said second signal and said first signal;

comparing said difference signal with a target signal; and determining a seasoning state of said plasma processing system from and comparing of said difference signal with said target signal, wherein said first and second signals are a product of multivariate analysis.

30. The method according to claim 29, wherein said loading said first substrate follows a maintenance operation performed on said plasma processing system.

31. The method according to claim 29, wherein said second substrate is an Nth substrate loaded into said plasma processing system since a last maintenance operation was performed on said plasma processing system.

32. The method according to claim 29, wherein said first and second signals are at least one of a light intensity, a spectral light intensity and light spectrum.

33. The method according to claim 29, wherein said multivariate analysis comprises principal components analysis.

34. The method according to claim 33, wherein a result of said principal components analysis includes a set of scores associated with said firs signal and a set of scores associated with said second signal.

35. The method according to claim 34, wherein said first signal is a distance between said set of scores associated with said first signal and an expected set of scores and said second signal is a distance between said set of scores associated with said second signal and an expected set of scores.

36. The method according to claim 35, wherein said determining said seasoning state of said plasma processing system comprises determining at said plasma processing system is seasoned when said difference signal is substantially close to a value of zero.

37. A detection system comprising:

a light detection device configured to be coupled to a plasma processing system to receive light emitted from a plasma;

a controller coupled to said light detection device, said controller configured to measure a signal related to the received light and to correlate a change between said signal and a target signal with a seasoning state of said plasma processing system herein the measured signal related to the received light is a product of multivariate analysis.

38. A method for constructing a seasoning model for a plasma processing system, said method comprises:

measuring a plurality of optical signals;

determining a first set of said plurality of optical signals corresponding to an unseasoned plasma processing system;

forming a second set of said plurality of optical signals by discarding aid first set of said plurality of optical signals; and performing principal components analysis on said second set of said plurality of said optical signals, wherein an output of said principal components analysis comprises said seasoning model.

39. The method for constructing a seasoning model as recited in claim 38, wherein said plurality of optical signals corresponds to a plurality of substrates.

40. The method for constructing a seasoning model recited in claim 38, wherein said seasoning model comprises a set of principal components and model scores.

41. The method for constructing a seasoning model recited in claim 38, wherein said determining a first set of said plurality of optical signal corresponding to an unseasoned plasma processing system comprises performing principal components analysis.

* * * * *